(12) United States Patent
Flohr et al.

(10) Patent No.: US 10,716,526 B2
(45) Date of Patent: Jul. 21, 2020

(54) X-RAY SYSTEM AND IMAGE RECONSTRUCTION METHOD

(71) Applicant: Siemens Healthcare GmbH, Erlangen (DE)

(72) Inventors: Thomas Flohr, Uehlfeld (DE); Steffen Kappler, Effeltrich (DE); Bernhard Krauss, Burgthann (DE); Bernhard Schmidt, Fuerth (DE); Friederike Schoeck, Erlangen (DE); Karl Stierstorfer, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 145 days.

(21) Appl. No.: 15/369,960

(22) Filed: Dec. 6, 2016

(65) Prior Publication Data

US 2017/0172532 A1    Jun. 22, 2017

(30) Foreign Application Priority Data

Dec. 22, 2015  (DE) .......................... 10 2015 226 489

(51) Int. Cl.
    *A61B 6/00* (2006.01)
    *A61B 6/03* (2006.01)
    *A61B 6/06* (2006.01)

(52) U.S. Cl.
    CPC ............ *A61B 6/5205* (2013.01); *A61B 6/032* (2013.01); *A61B 6/405* (2013.01); *A61B 6/4007* (2013.01);
    (Continued)

(58) Field of Classification Search
    CPC ..... A61B 6/4241; A61B 6/482; A61B 6/4014; A61B 6/4035; A61B 6/06; A61B 6/032;
    (Continued)

(56) References Cited

U.S. PATENT DOCUMENTS 9,448,325 B2 *  9/2016  Chen ..................... A61B 6/032
9,662,078 B2 *  5/2017  Berglund ............. A61B 6/4233
(Continued)

FOREIGN PATENT DOCUMENTS

| CN | 102076263 A | 5/2011 |
| DE | 102006015356 A1 | 8/2007 |
| DE | 102007027460 A1 | 12/2008 |

OTHER PUBLICATIONS

German Office Action dated Sep. 21, 2016.
First Office Action dated Jul. 26, 2019 in Chinese Application No. 201611195593.7.

*Primary Examiner* — David J Makiya
*Assistant Examiner* — Soorena Kefayati
(74) *Attorney, Agent, or Firm* — Harness, Dickey & Pierce, P.L.C.

(57) ABSTRACT

An X-ray system, in particular a computed tomography system, for acquiring projection data of an examination subject includes one or more X-ray radiation sources, at least one of the one or more X-ray radiation sources including at least one prefilter, the one or more X-ray radiation sources being configured to generate X-ray radiation including at least two X-ray radiation spectra, the at least one prefilter being configured to at least one of spatially distribute or temporally modify the X-ray radiation, and a one or more photon-counting detectors configured to detect the X-ray radiation passing through the examination subject in an energy-resolved manner according to at least two detection thresholds, and generate projection data based on the detection.

22 Claims, 2 Drawing Sheets

(52) U.S. Cl.
CPC .......... *A61B 6/4014* (2013.01); *A61B 6/4035* (2013.01); *A61B 6/4208* (2013.01); *A61B 6/4241* (2013.01); *A61B 6/482* (2013.01); *A61B 6/504* (2013.01); *A61B 6/54* (2013.01); *A61B 6/06* (2013.01); *A61B 6/508* (2013.01)

(58) Field of Classification Search
CPC ..... A61B 6/4007; A61B 6/7014; A61B 6/405; A61B 6/4208; A61B 6/504; A61B 6/508; A61B 6/5205; A61B 6/54
See application file for complete search history.

(56) References Cited

U.S. PATENT DOCUMENTS

| | | | | |
|---|---|---|---|---|
| 9,980,686 B2* | 5/2018 | Proksa | | A61B 6/4233 |
| 2003/0053597 A1* | 3/2003 | Flohr | | A61B 6/032 378/156 |
| 2003/0195416 A1* | 10/2003 | Toth | | A61B 6/032 600/427 |
| 2006/0062353 A1* | 3/2006 | Yatsenko | | A61B 6/032 378/156 |
| 2006/0251209 A1* | 11/2006 | Tkaczyk | | A61B 6/4241 378/5 |
| 2007/0147574 A1* | 6/2007 | Bernard De Man | | A61B 6/4241 378/4 |
| 2007/0183560 A1* | 8/2007 | Popescu | | A61B 6/032 378/5 |
| 2010/0310042 A1* | 12/2010 | Fox | | A61B 6/4241 378/53 |
| 2011/0096892 A1* | 4/2011 | Forthmann | | A61B 6/032 378/5 |
| 2011/0098892 A1 | 4/2011 | Lundmark et al. | | |
| 2011/0261923 A1* | 10/2011 | Schmitt | | G21K 1/10 378/8 |
| 2012/0187312 A1* | 7/2012 | Guez | | A61B 6/4035 250/492.1 |
| 2012/0236987 A1* | 9/2012 | Ruimi | | A61B 6/032 378/19 |
| 2015/0297155 A1* | 10/2015 | Christensen | | A61B 6/032 378/5 |
| 2015/0305697 A1* | 10/2015 | Tamura | | A61B 6/032 378/5 |
| 2015/0312998 A1* | 10/2015 | Tamura | | A61B 6/482 378/5 |
| 2016/0073982 A1* | 3/2016 | Sasov | | A61B 6/4035 378/16 |
| 2016/0113617 A1* | 4/2016 | Herrmann | | A61B 6/42 378/207 |
| 2017/0119337 A1* | 5/2017 | Nekovar | | A61B 6/5288 |
| 2017/0273642 A1* | 9/2017 | Engel | | A61B 6/4007 |

* cited by examiner

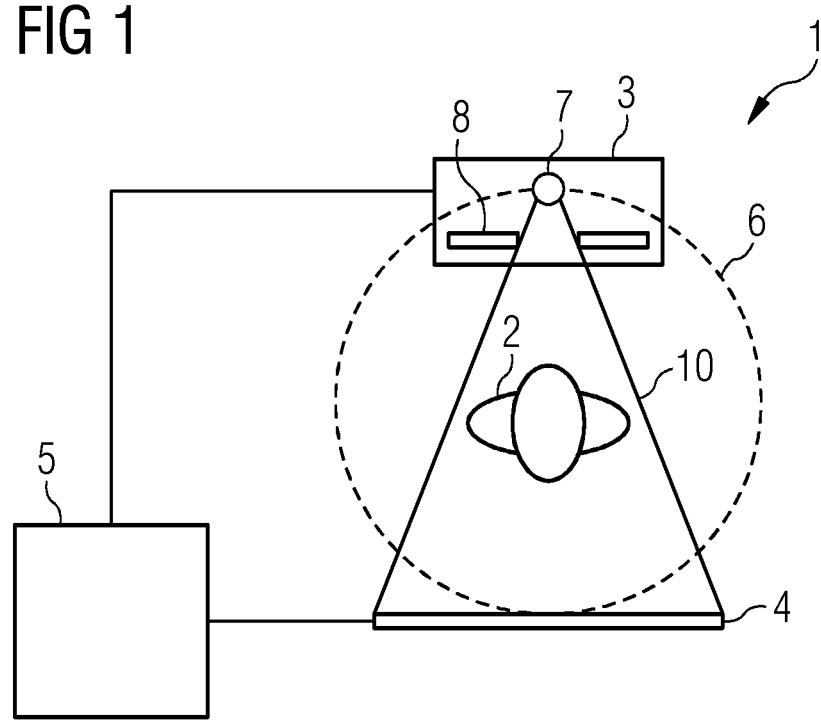
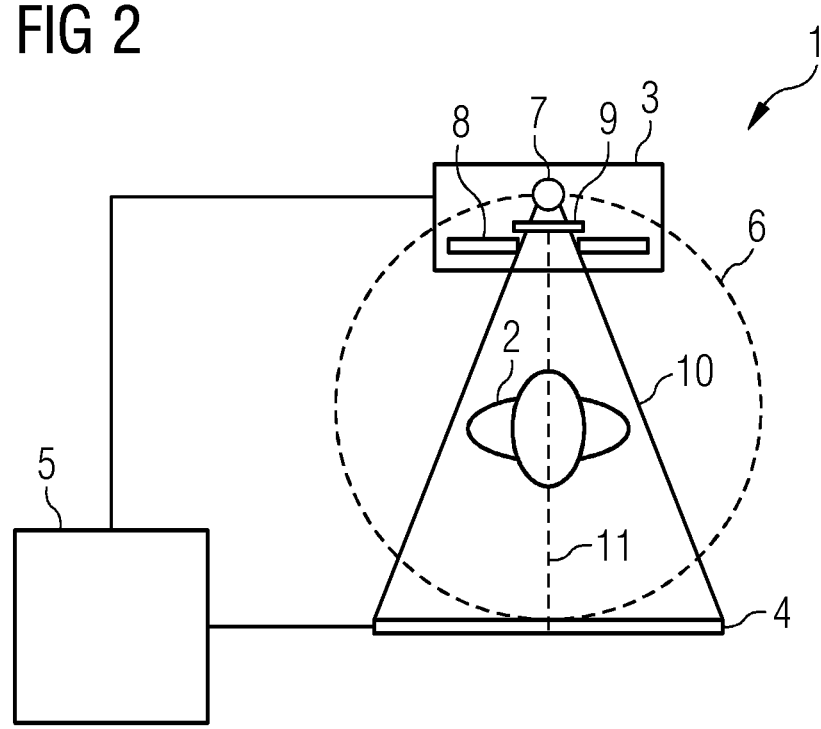

X-RAY SYSTEM AND IMAGE RECONSTRUCTION METHOD

PRIORITY STATEMENT

The present application hereby claims priority under 35 U.S.C. § 119 to German patent application number DE 102015226489.0 filed Dec. 22, 2015, the entire contents of which are hereby incorporated herein by reference.

FIELD

At least one embodiment of the invention generally relates to an X-ray system for the acquisition of projection data and/or to an image reconstruction method.

BACKGROUND

When X-ray radiation is projected through an examination subject, different absorption or scatter characteristics result as a function of the spectrum used and the substances that are to be penetrated, the proportion of low energies in the spectrum in relation to the high energies being absorbed more rapidly (beam hardening). With regard to the contrast or noise of the images that are to be reconstructed, it may therefore be advantageous to adapt the spectrum used to fit the planned projection through the examination subject. Basically, two approaches come into consideration for this purpose: On the one hand, the emitted spectrum may be regulated by way of the source, while on the other hand the detector may be embodied and if necessary be amenable to regulation, for example by means of filters, in such a way that it detects only defined ranges of a relatively wide incoming spectrum. An indicator for the spectral separation in this case is the spectral sensitivity distribution, which is given by the product yielded from the spectrum and the sensitivity of the detector.

A number of approaches for how the spectrum may be modified on the source side are known from real-world practice. These multi-energy techniques, as they are known, are categorized into the variants briefly described below. With so-called "kV switching", the tube voltage, also known as the acceleration voltage, is varied at short time intervals over one or more readout cycles such that the electrons absorb different energies, finally resulting as bremsstrahlung ("braking radiation") in different X-ray spectra. The "dual spiral" variant involves two scans of the same subject region which are performed using different X-ray spectra. The "split filter" approach represents a further variant, the prefilter of which consists of two different materials which allow different X-ray spectra to pass through. The X-ray radiation is then detected in each case only in the detector elements that are associated with the corresponding prefilter. Also known from real-world practice is the so-called "dual source" technique, in which two tube-detector systems generate the X-ray radiation simultaneously with different X-ray spectra and measure these separately from one another.

Previously, the projection data was acquired in most cases using detectors which integrate across the entire energy range, referred to as the total spectrum, of the X-ray radiation in order to acquire measurement data. In order to achieve a certain energy resolution, the detectors may also be arranged in two layers as a "dual layer detector", with predominantly the low-energy quanta being detected in the first layer and the remaining higher-energy X-ray quanta being detected in the second layer.

In contrast thereto, photon-counting detectors measure the input spectrum in a spectrally resolved manner. In this case, depending on the number of thresholds implemented, a plurality of spectrally different datasets are generated. Because there is only one input spectrum, however, the spectral separation of the individual datasets may in this case be less good than in the case of the previously described multi-energy approaches. The use of such a photon-counting detector in an imaging system is described in the publication DE 102007027460 A1.

SUMMARY

At least one embodiment of the present invention discloses an X-ray system and an image reconstruction method providing improved spectral separation.

At least one embodiment is directed to an X-ray system and at least one embodiment is directed to an image reconstruction method.

For the acquisition of projection data of an examination subject, the X-ray system of at least one embodiment comprises an X-ray emitter arrangement comprising a number of X-ray radiation sources and a number of photon-counting detectors having at least two detection thresholds. In this configuration, the number of X-ray radiation sources are embodied in such a way that they generate X-ray radiation having at least two X-ray radiation spectra. Furthermore, the number of photon-counting detectors are arranged and embodied in such a way that they detect at least the X-ray radiation passing through the examination subject in an energy-resolved manner in the form of projection data.

In at least one embodiment, a method for image reconstruction via an X-ray system comprises the following. In a first step, X-ray radiation having at least two X-ray radiation spectra is generated via an X-ray emitter arrangement comprising a number of X-ray radiation sources. In a second step, at least the X-ray radiation penetrating through the examination subject is detected via a number of photon-counting detectors in the form of energy-resolved projection data. In a third step, an image is reconstructed on the basis of the projection data of the examination subject.

An implementation largely in software has the advantage that control devices that have already been in use can easily be retrofitted by way of a software update in order to operate in the inventive manner. In that respect, at least one embodiment is directed to a corresponding computer program product comprising a computer program which can be loaded directly into a memory device of a control device of an X-ray system, having program sections for performing all steps of at least one embodiment of the inventive method when the program is executed in the control device. As well as the computer program, such a computer program product may also comprise additional constituent parts such as e.g. documentation and/or additional components, including hardware components, such as e.g. hardware keys (dongles, etc.) to allow use of the software.

At least one embodiment is directed to a non-transitory memory device of a control device of an X-ray system, storing a computer program including program sections for performing at least one embodiment of the method when the computer program is executed in the control device of the X-ray system.

A computer-readable medium, for example a memory stick, a hard disk or some other transportable or permanently installed data carrier, on which the program sections of the computer program that can be read in and executed by a computer unit of the control device are stored, may be used in at least one embodiment for transporting the computer program to the control device and/or for storing the same on or in the control device. For this purpose, the computer unit may have e.g. one or more cooperating microprocessors or the like.

Other particularly advantageous embodiments and developments of the invention will become apparent from the dependent claims as well as from the following description, wherein the independent claims of one claims category may also be developed analogously to the dependent claims of a different claims category and in particular also individual features of different example embodiments or variants may be combined to create new example embodiments or variants.

BRIEF DESCRIPTION OF THE DRAWINGS

The invention is explained once again below in more detail with the aid of example embodiments and with reference to the attached figures. Like components are labeled with the same reference numerals in the various figures. The figures are generally not drawn to scale. In the figures:

FIG. 1 shows a roughly schematic representation of an example embodiment of an X-ray system according to the invention using kV switching, FIG. 2 shows a roughly schematic representation of an example embodiment of an X-ray system according to the invention using a split filter.

DETAILED DESCRIPTION OF THE EXAMPLE EMBODIMENTS

Figure 3:
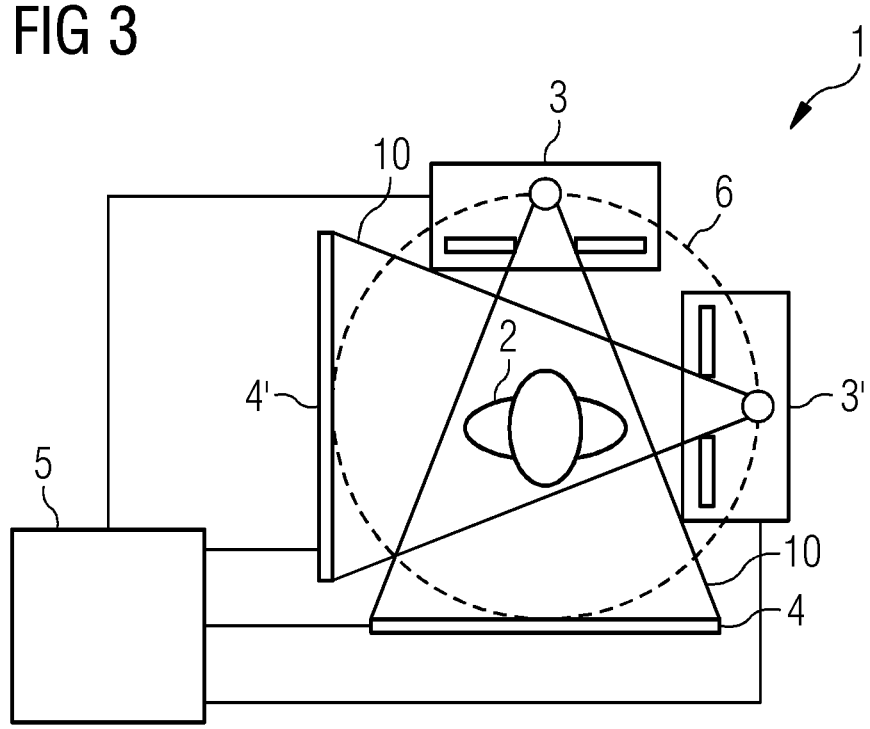
FIG. 3 shows a roughly schematic representation of an example embodiment of an X-ray system according to the invention using dual-source.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

For the acquisition of projection data of an examination subject, the X-ray system of at least one embodiment comprises an X-ray emitter arrangement comprising a number of X-ray radiation sources and a number of photon-counting detectors having at least two detection thresholds. In this configuration, the number of X-ray radiation sources are embodied in such a way that they generate X-ray radiation having at least two X-ray radiation spectra. Furthermore, the number of photon-counting detectors are arranged and embodied in such a way that they detect at least the X-ray radiation passing through the examination subject in an energy-resolved manner in the form of projection data.

What is understood by the term "X-ray system" is preferably a computed tomography system, though it may also include a simple X-ray machine or an angiography device. It will therefore be applied in the following without loss of generality also to a computed tomography system. The subject that is to be examined may be an object or an animal, though preferably it will be a human patient.

In at least one embodiment, the X-ray emitter arrangement of the X-ray system comprises one or two X-ray radiation sources. The X-ray radiation source in turn comprises an X-ray tube and therefore constitutes the beam generating unit. Further elements, such as, for example, collimators, filters, shutters or the like, may also be encompassed by the unit. The term X-ray radiation spectrum—spectrum for short—is equivalent to an amount of emitted radiation having a distribution of different energies or wavelengths which is generated in an X-ray radiation source as bremsstrahlung. In this case the spectrum is often characterized by the voltage present in the X-ray tube, for example 140 kV or the like. The fact that the X-ray emitter arrangement is embodied with the number of X-ray radiation sources for generating X-ray radiation with at least two spectra means that either a single X-ray radiation source is able to generate at least two, preferably different, spectra or a plurality of X-ray radiation sources generate the preferably different spectra. Even with a plurality of X-ray radiation sources, therefore, each individual source may be embodied for generating different spectra.

In addition to the X-ray radiation sources, the X-ray system preferably comprises one or two photon-counting detectors. These in turn comprise preferably a sensor array of semiconductor sensors, e.g. made from silicon (Si), cadmium telluride (CdTe) or cadmium zinc telluride (CZT), which convert the incident photons directly into an electrical signal. The photons are preferably detected locally over the sensor array, i.e. in a spatially resolved manner, and are sorted simultaneously as a function of their energy into groupings known as bins. The semiconductor sensors can therefore detect the light quanta separately for at least two different energy ranges. Energy thresholds may be specified as necessary for the purpose of the sorting and set electronically by way of a control device. This enables the individual detectors to be adapted to fit the requirements of the examination. The electrical signals, which in their totality represent the projection data, are then forwarded to an evaluation unit. The latter may be incorporated in the control unit and be implemented in a computer unit, for example.

Projection data of the examination subject is acquired by the number of detectors. The data therefore indicates in a spatially resolved manner the intensity and the energy distribution of the X-ray radiation which is projected as a defined spectrum through the examination subject onto the detector by the number of X-ray radiation sources in the main irradiation direction. In the process the X-ray radiation may be absorbed and/or scattered locally differently by the examination subject, depending on the thickness and material of the latter. As a result, in the logical inversion, the projection data contains local information about the examination subject. The energy distribution of the X-ray radiation arriving at the detector behind the examination subject, i.e. the energy distribution of the projection, is in this case measured by way of the detection thresholds of the spatially and energy resolving detectors. Thus, the projection data, which is to be understood as raw data, may form a basis for generating image data of the examination subject. In this case the projection data may preferably be assigned to the respective spectrum emitted by the X-ray radiation source. The projection data therefore comprises information about the spectrum used on the source side, spatial information, and information about the main irradiation direction and about the energy of the individual photons that is deposited in the detector.

In contrast to the prior art, the X-ray system according to at least one embodiment of the invention therefore combines the known multi-energy techniques with a photon-counting detector, and not with energy-integrating detectors. This enables a better spectral separation, i.e. a finer segmentation of the X-ray spectrum detected for the imaging, to be achieved, since the spectrum is subdivided into ranges both on the source side during the emission and on the detector side during the detection. The ultimate effect of this is an improvement in imaging.

In at least one embodiment, a method for image reconstruction via an X-ray system comprises the following. In a first step, X-ray radiation having at least two X-ray radiation spectra is generated via an X-ray emitter arrangement comprising a number of X-ray radiation sources. In a second step, at least the X-ray radiation penetrating through the examination subject is detected via a number of photon-counting detectors in the form of energy-resolved projection data. In a third step, an image is reconstructed on the basis of the projection data of the examination subject.

Preferably, an X-ray system according to at least one embodiment of the invention is used for performing the method. The X-ray system can be controlled automatically by way of a control device, with the aid of a specified examination protocol, for example, and/or settings of the individual parameters required for the examination can be entered by an operator via an input interface. In particular, the X-ray spectra used and the detection thresholds can be specified at this time. Following the acquisition, the projection data can be transmitted directly to an evaluation unit and/or stored in a buffer, in which the projection data is stored as raw data. The image reconstruction step can therefore be performed immediately or at a later time, as requirements dictate. In the course of the reconstruction, in which known image generation methods appropriately modified to achieve a finer spectral resolution are applied, an image of the examination subject is generated on the basis of the projection data of the examination subject. This may be an image representing the examination subject, e.g. in the form of sectional images (slices), 3D images or even 4D image data (with a temporal component). The image may in this case be represented in grayscale levels or may also be highlighted in color according to a material or tissue composition, the composition being determined on the basis of the projection data. This is particularly advantageous for the detection of calcifications of blood vessels, contrasted objects and/or tumors.

An implementation largely in software has the advantage that control devices that have already been in use can easily be retrofitted by way of a software update in order to operate in the inventive manner. In that respect, at least one embodiment is directed to a corresponding computer program product comprising a computer program which can be loaded directly into a memory device of a control device of an X-ray system, having program sections for performing all steps of at least one embodiment of the inventive method when the program is executed in the control device. As well as the computer program, such a computer program product may also comprise additional constituent parts such as e.g. documentation and/or additional components, including hardware components, such as e.g. hardware keys (dongles, etc.) to allow use of the software.

A computer-readable medium, for example a memory stick, a hard disk or some other transportable or permanently installed data carrier, on which the program sections of the computer program that can be read in and executed by a computer unit of the control device are stored, may be used in at least one embodiment for transporting the computer program to the control device and/or for storing the same on or in the control device. For this purpose, the computer unit may have e.g. one or more cooperating microprocessors or the like.

Other particularly advantageous embodiments and developments of the invention will become apparent from the dependent claims as well as from the following description, wherein the independent claims of one claims category may also be developed analogously to the dependent claims of a different claims category and in particular also individual features of different example embodiments or variants may be combined to create new example embodiments or variants.

In a variant of the X-ray system according to at least one embodiment of the invention, an X-ray radiation source for generating the X-ray radiation with at least two X-ray radiation spectra is embodied in such a way that it switches between different acceleration voltages (X-ray voltages) under the control of a control device. In this case the X-ray radiation is detected by the photon-counting detectors in synchronism with the changeover of the acceleration voltages. With this variant, known as kV switching, the spectrum of the emitted X-ray radiation may therefore be modified already at the time of its generation solely by way of the regulation of the tube voltage. Preferably, the tube voltage alternates at high frequency, e.g. 1000 Hz, between two specified values, e.g. 80 kV and 140 kV. The data recorded from regions in which the X-ray radiation does not pass through the examination subject may advantageously be used in this case for synchronizing the detection and for the alignment with the originally emitted spectra. This is because the data substantially, i.e. apart from the effect of the ambient air, exactly reflects the spectrum emitted by the X-ray radiation source.

In a further variant of the X-ray system according to at least one embodiment of the invention, at least one of the X-ray radiation sources for generating the X-ray radiation with at least two X-ray radiation spectra comprises at least one prefilter. The prefilter may be embodied for example as a plate made of light or heavy metal in order to absorb the soft and medium-soft X-ray beams. A prefilter of this form therefore essentially hardens the beam, since primarily the X-ray radiation having less penetrating, greater wavelengths is filtered out by it. Already by means of a prefilter it is thus possible to generate two different X-ray spectra, namely the spectrum actually generated by the X-ray tube and the spectrum modified by means of the prefilter. Two possible applications of this effect are described in the following sub-variants.

In the case of the first, and preferred, sub-variant of the X-ray system according to at least one embodiment of the invention, the at least one prefilter spatially distributes ranges of an X-ray radiation spectrum to defined angular ranges of the photon-counting detectors. For this purpose the prefilter has filter sections made of different materials which allow different spectra to pass through. The radiation emitted by these so-called "split filters" is accordingly emitted over the filter sections at certain angular ranges such that finally it also impinges on dedicated areas of the sensor array of the detector which by means of their arrangement are assigned to the respective spectrum. If, for example, an arrangement comprised of X-ray radiation source and detector now rotates on a circular path around the examination subject and all filter sections are located on the circular path, then complete projection data of the examination subject is acquired for all of the spectra generated by means of the prefilter. In the case of filter sections arranged orthogonally to the circular path, i.e. in the direction of the axis of rotation, the projection data can be acquired for example in different revolutions when the respective region of the examination subject is overswept multiple times in accordance with the filter sections during axial displacement in a spiral scan. Particularly preferably, the prefilter comprises two filter sections.

In the second sub-variant of the X-ray system according to at least one embodiment of the invention, the at least one prefilter temporally modifies the X-ray radiation spectrum, which is detected in a synchronized manner by the photon-counting detectors. As in the case of the previously described kV switching, the spectrum is varied here with respect to time. This can be achieved for example by periodic, rapid insertion and removal of the prefilter into and out of the beam path, respectively. Alternatively, it also possible to switch between different prefilters. The synchronization can also be carried out analogously to the kV switching.

In principle, the two above-described sub-variants may also be combined with one another. Basically, therefore, spatially separated and temporally modified spectra may be generated simultaneously for example by means of suitable prefilters arranged in series in order to achieve an even finer energetic segmentation of the spectra.

A further variant of the X-ray system according to at least one embodiment of the invention comprises a control device which is embodied in such a way that it controls an X-ray radiation source and the number of photon-counting detectors such that projection data is acquired using different X-ray radiation spectra in at least two scans. In this case the different X-ray radiation spectra are generated by means of different acceleration voltages of the X-ray radiation source. In this variant, known as "dual spiral", the X-ray spectrum of an X-ray tube is therefore varied by way of the tube voltage in a similar manner as in the case of kV switching. Unlike in the case of kV switching, however, the voltage is not switched at high frequency, but remains constant, e.g. 80 kV, for a scan operation and is regulated to a different constant value, e.g. 140 kV, for the at least one sequential scan.

In a further variant of the X-ray system according to at least one embodiment of the invention, the X-ray emitter arrangement has at least two X-ray radiation sources which are embodied in such a way that they generate different X-ray radiation spectra. The different spectra of the at least two X-ray radiation sources can in this case be generated by means of different acceleration voltages and/or different filters. Just one large detector having detection zones that are assigned to the individual X-ray radiation sources may in fact be embodied for the at least two X-ray radiation sources. Preferably, however, each X-ray radiation source is assigned a dedicated detector. Particularly preferably, the X-ray system has precisely two X-ray radiation sources, preferably arranged roughly orthogonally to one another, each having a respective assigned detector. This variant advantageously permits completely separated X-ray spectra to be generated and these also to be detected by means of separate detectors. In combination with the photon-counting detectors, a particularly good spectral separation is achieved as a result.

In a preferred example embodiment of the X-ray system according to the invention, at least one of the photon-counting detectors has at least four, preferably at least six, detection thresholds. A higher number of detection thresholds enables the X-ray spectrum to be segmented further, which makes for an additional improvement of the spectral separation.

In a preferred embodiment variant of an image reconstruction method according to the invention, the projection data is assigned to the respective X-ray spectrum. That is to say that the spectrum emitted by the X-ray radiation source can be linked with the values in the projection data acquired by the detector on the basis of the energy values per se and/or the spatial separation and/or temporal synchronization. On the basis of the projection data it is therefore possible to trace with which emitted spectrum the detected energy or intensity values were generated.

In the image reconstruction according to at least one embodiment of the invention, the projection data assigned to the X-ray spectra is preferably combined to form an optimized image. The optimization of the image can be performed on the basis of different criteria. For example, specific regions may be selected from the projection data of the examination subject, in which regions e.g. blood vessels, bones or organs are located which are optimally represented using projection data from a specific spectral range. However, the optimization may also be performed having regard to parameters such as contrast, noise or the like.

FIG. 1 shows by way of example and in a roughly schematic view an inventive X-ray system 1 as a computed tomography system 1 in a variant using kV switching. Since a computed tomography system represents the preferred embodiment variant of the X-ray system according to the invention, the following explanations relate, without loss of generality, to a computed tomography system 1. The computed tomography system 1 in this case comprises an X-ray emitter arrangement comprising an X-ray radiation source 3, a detector 4 and a control device 5. The X-ray radiation source 3 and the detector 4 are connected to the control device 5. The X-ray radiation source 3 and the detector 4 are free to move and are arranged diametrically to one another on a circular path 6. They therefore stand in a fixed positional relationship to one another in which the detector detects the radiation emitted by the X-ray radiation source 3, and they thus form a first source-detector arrangement. A patient 2 is located as examination subject in the center of the circular path 6. The X-ray radiation source 3 comprises an X-ray tube 7 and a collimator 8. The collimator is arranged spaced apart at a slight distance from the X-ray tube 7 on a side of the X-ray tube 7 facing toward the patient 2. An exit angle of X-ray radiation 10 that is emitted by the X-ray tube 7 during operation can be set via the collimator.

During operation, the X-ray radiation source 3 and the detector 4 are rotated around the patient 2 on the circular path 6 for the purpose of acquiring projection data. At the same time the acceleration voltage of the X-ray radiation source 3 is varied by alternating in a stepped manner, regulated by the control device 5 for example, between values of 80 kV and 140 kV at a frequency of, for example, 1000 Hz. The acceleration voltage therefore alternates rapidly compared with the rotational movement of the detector 4 and the X-ray radiation source 3, which takes place on the circular path at a maximum frequency of typically approx. 4 Hz. Different X-ray spectra are generated in the X-ray tube 7 by the alternating acceleration voltage. The spectra pass through the patient as X-ray radiation 10 at the exit angle defined by way of the collimator 8. They subsequently impinge on the energy-resolving detector 4. The latter therefore records measured values of X-ray projections of the patient which are generated by means of different X-ray spectra. Thus, projection data is acquired from different angular positions relative to the patient and can be assigned with respect to time to the spectrum emitted by the X-ray tube. The acquired projection data can then be transmitted to an evaluation unit located for example in the control device 5 and reconstructed there to produce an image B of the patient 2. In order to acquire projection data from other regions of the patient 2, the patient 2 can be moved relative to the computed tomography system 1, for example by means of a positionable patient table (not shown here), perpendicularly to the plane of the circular path 6. In the case of the variant called spiral CT, the acquisition takes place continuously while the table is likewise advanced continuously.

FIG. 2 shows by way of example and in a roughly schematic view an embodiment of an inventive computed tomography system 1 in the split-filter variant. In addition to the X-ray system 1 illustrated in FIG. 1, a prefilter 9 is inserted in this case between X-ray tube 7 and collimator 8. The prefilter comprises two materials having different properties in terms of their X-ray absorption. The X-ray radiation generated by the X-ray tube 7 is therefore prefiltered differently according to material and exits the X-ray radiation source in the form of two different X-ray spectra. These are spatially separated, for example into a low-energy and a high-energy spectrum, along a dividing line 11 corresponding to the boundary between the materials of the prefilter. Subsequently, the X-ray radiation 10 of the two spectra projected through the patient 2 onto the detector 5 is detected, also in a spatially separated manner, in different sections of the detector and can thus be assigned to the respective emitted spectrum. Alternatively, the filter 9 may also be arranged rotated through 90°, such that the dividing line 11 divides the different spectra in the image plane, as it were. With this alternative, the projection data for both spectra is acquired sequentially with the table feed for the regions of the patient 2 that are to be recorded. In contrast to FIG. 1, in this case the acceleration voltage does not have to be varied, apart from which the acquisition of the projection data in this case takes place substantially analogously to the variant in FIG. 1.

FIG. 3 shows by way of example and in a roughly schematic view a computed tomography system 1 according to the invention in a dual-source variant. In addition to the system illustrated in FIG. 1, in this case the computed tomography system 1 has a second source-detector arrangement comprising a second X-ray radiation source 3' and an associated second detector 4'. In this configuration, the X-ray emitter arrangement therefore comprises two X-ray radiation sources 3, 3'. As in the first source-detector arrangement, the X-ray radiation source 3' and the detector 4' are arranged diametrically opposite one another on the circular path 6, but are oriented orthogonally to the first source-detector arrangement. The second source-detector arrangement is also free to move on the circular path 6, though it remains stationary relative to the first source-detector arrangement, since both source-detector arrangements are e.g. typically arranged jointly in a gantry rotating on the circular path 6. Different acceleration voltages are present in each case at the X-ray tubes of the first and the second source-detector arrangement in order to emit different spectra. Alternatively, the spectrum of one X-ray radiation source could also be modified by way of a prefilter. Apart from the constant acceleration voltages, the acquisition of the projection data proceeds in this case also substantially analogously to FIG. 1.

Figure 4:
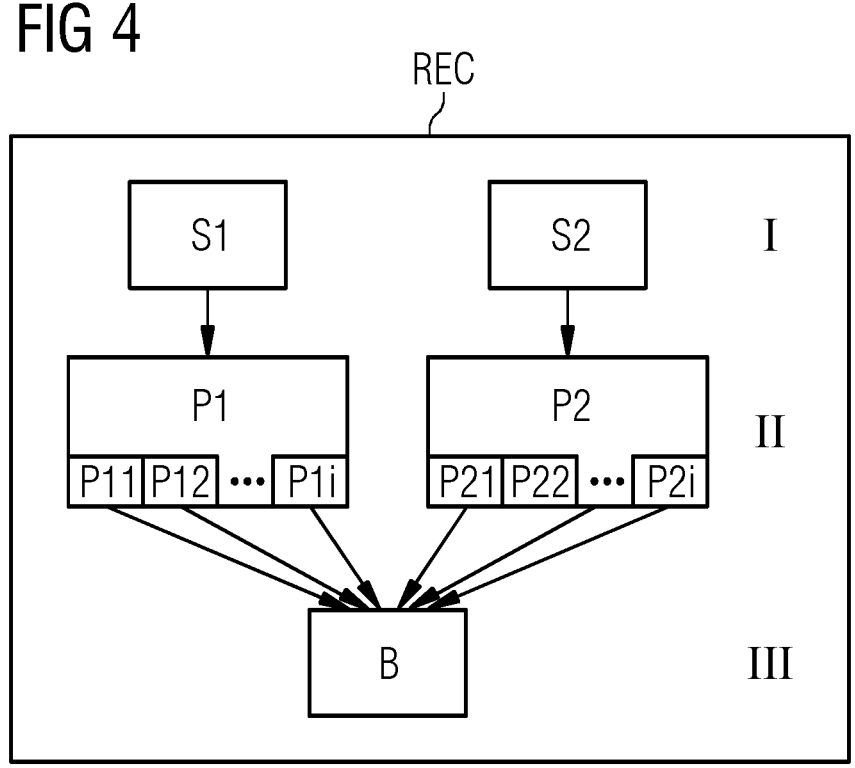
FIG. 4 shows a block diagram of a workflow of an example embodiment of a method according to the invention.

FIG. 4 shows by way of example a workflow of an inventive image reconstruction REC in the form of a block diagram. In a first step I of the method, X-ray radiation S1 having a first defined spectrum and X-ray radiation S2 having a second defined spectrum are generated in a preferably inventive computed tomography system 1, as has already been described above. That is to say that the radiation S1 has an energy distribution that diverges from the radiation S2. At least some of the radiation S1, S2 passes through an examination subject 2 and is detected as a projection of the examination subject 2 by at least one energy-resolving detector 4 in the second step II. According to the method, this may be precisely one detector, in which case the detection for the radiation S1 takes place spatially, temporally and/or even via the spectra themselves separately from the detection of the radiation S2. Alternatively, the detection of the radiation S1 may also be realized by way of a first detector 4, and the detection of the radiation S2 by way of a separate second detector. Accordingly, the projection data P1 is assigned to the X-ray radiation S1 having the first defined spectrum. An analogous procedure is followed with the projection data P2, which is assigned to the second defined spectrum.

During the detection, however, the projection data P1 and the projection data P2 are segmented still further, specifically on the basis of the energy distribution of the projection, into energy-resolved projection data P11, P12, . . . , P1$i$, P21, P22, . . . , P2$i$. The projection data P11, P12, . . . , P1$i$ is in this case assigned to the first spectrum, and the projection data P21, P22, . . . , P2$i$ is assigned to the second spectrum. The projection data P11 is furthermore the data of the first spectrum from a defined energy range of the X-ray radiation projected through the examination subject 2, namely the energy range that is acquired in a first bin of the energy-selective detector 4. The same applies analogously up to and including the projection data P2$i$, which is acquired in the i-th bin and is assigned to the second spectrum. The bins of the detector 4 therefore acquire data of a defined energy range of the projection in each case. The limits of the energy ranges of the bins can be specified, for example by way of a control protocol or by an operator, and set with the aid of the control device 5. Further steps in the acquisition are performed analogously to the methods already established in computed tomography.

The projection data accordingly contains information about the generating spectrum and about the energy distribution present in the projection. In the third step III, images can be generated from this spectrally separated projection data for the individual energy ranges using known reconstruction algorithms in each case. These images can then be merged with one another according to requirements in order to highlight certain materials or tissue as desired and to optimize the same in terms of contrast and/or noise and/or contrast-noise ratio. Finally, by virtue of the better spectral separation, the inventive method REC delivers an improved representation of the reconstructed image B.

In conclusion, it is pointed out once again that the devices and methods described in detail in the foregoing are merely example embodiments which may be modified in the widest variety of ways by the person skilled in the art without leaving the scope of the invention. Furthermore, the use of the indefinite articles "a" or "an" does not preclude the possibility that the features in question may also be present in a plurality. Equally, the term "element" does not preclude the possibility that the component in question may consist of a plurality of cooperating subcomponents, which, according to circumstances, may also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray system for acquiring projection data of an examination subject, comprising:
    one or more photon-counting detectors; and
    one or more X-ray radiation sources, at least one of the one or more X-ray radiation sources including at least one prefilter, the one or more X-ray radiation sources being configured to generate X-ray radiation including at least two X-ray radiation spectra, the at least one prefilter being configured to both spatially and temporally distribute the X-ray radiation such that different spectra among the at least two X-ray radiation spectra are distributed to each of a plurality of different defined angular ranges at different times, each of the plurality of different defined angular ranges corresponding to respective subsets of the one or more photon-counting detectors,
    wherein the one or more photon-counting detectors is configured to
        detect the X-ray radiation passing through the examination subject in an energy-resolved manner according to at least two detection thresholds, and
        generate projection data based on the detection.

2. The X-ray system of claim 1, wherein each of the one or more X-ray radiation sources is configured to
    generate the X-ray radiation including the at least two X-ray radiation spectra; and
    switch between different acceleration voltages,
    wherein the X-ray radiation is detectable in a synchronized manner by respective ones of the one or more photon-counting detectors.

3. The X-ray system of claim 1, wherein the at least one prefilter is configured to temporally modify the X-ray radiation by selectively filtering the X-ray radiation according to time in synchronization with the one or more photon-counting detectors.

4. The X-ray system of claim 1, further comprising:
    a control device configured to control the one or more X-ray radiation sources and the one or more photon-counting detectors such that the projection data is generated using a different spectrum of the at least two X-ray radiation spectra in each of at least two scans, the different spectrum being generated via a different acceleration voltage of the one or more X-ray radiation sources.

5. The X-ray system of claim 1, wherein the one or more X-ray radiation sources includes at least two X-ray radiation sources, each of the at least two X-ray radiation sources being configured to generate a different X-ray radiation spectrum of the at least two X-ray radiation spectra.

6. The X-ray system of claim 1, wherein the at least two detection thresholds include at least four detection thresholds.

7. The X-ray system of claim 1, wherein the X-ray system is a computed tomography system.

8. The X-ray system of claim 2, wherein the at least one prefilter is configured to temporally modify the X-ray radiation by selectively filtering the X-ray radiation according to time in synchronization with the one or more photon-counting detectors.

9. The X-ray system of claim 2, further comprising:
a control device configured to control the one or more X-ray radiation sources and the one or more photon-counting detectors such that the projection data is generated using a different spectrum of the at least two X-ray radiation spectra in each of at least two scans, the different spectrum being generated via a different acceleration voltage of the one or more X-ray radiation sources.

10. The X-ray system of claim 2, wherein the one or more X-ray radiation sources includes at least two X-ray radiation sources, each of the at least two X-ray radiation sources being configured to generate a different X-ray radiation spectrum of the at least two X-ray radiation spectra.

11. The X-ray system of claim 2, wherein the at least two detection thresholds include at least four detection thresholds.

12. The X-ray system of claim 4, wherein the at least one prefilter is configured to temporally modify the X-ray radiation by selectively filtering the X-ray radiation according to time in synchronization with the one or more photon-counting detectors.

13. The X-ray system of claim 4, wherein the one or more X-ray radiation sources includes at least two X-ray radiation sources, each of the at least two X-ray radiation sources being configured to generate a different X-ray radiation spectrum of the at least two X-ray radiation spectra.

14. The X-ray system of claim 4, wherein the at least two detection thresholds include at least four detection thresholds.

15. The X-ray system of claim 5, further comprising:
a control device configured to control the one or more X-ray radiation sources and the one or more photon-counting detectors such that the projection data is generated using a different spectrum of the at least two X-ray radiation spectra in each of at least two scans, the different spectrum being generated via a different acceleration voltage of the one or more X-ray radiation sources.

16. A method for image reconstruction, via an X-ray system, the method comprising:
generating X-ray radiation, including at least two X-ray radiation spectra, via one or more X-ray radiation sources, at least one of the one or more X-ray radiation sources including at least one prefilter, the at least one prefilter being configured to both spatially and temporally distribute the X-ray radiation such that different spectra among the at least two X-ray radiation spectra are distributed to each of a plurality of different defined angular ranges at different times, each of the plurality of different defined angular ranges corresponding to respective subsets of one or more photon-counting detectors;
energy-resolved detecting the X-ray radiation passing through an examination subject via the one or more photon-counting detectors to generate projection data of the examination subject; and
reconstructing an image based on the projection data of the examination subject.

17. The image reconstruction method of claim 16, wherein the projection data is assigned to a respective spectrum of the at least two X-ray radiation spectra.

18. A non-transitory memory device of a control device of the X-ray system, storing a computer program including program sections for performing the method of claim 16 when the computer program is executed in the control device of the X-ray system.

19. A non-transitory computer-readable medium storing program sections, readable and executable by a computer unit, to perform the method of claim 16 when the program sections are executed by the computer unit.

20. The image reconstruction method of claim 17, wherein during the reconstructing, the projection data assigned to each of the at least two X-ray radiation spectra is combined to form an improved image.

21. A non-transitory computer-readable medium storing program sections, readable and executable by a computer unit, to perform the method of claim 17 when the program sections are executed by the computer unit.

22. A non-transitory computer-readable medium storing program sections, readable and executable by a computer unit, to perform the method of claim 20 when the program sections are executed by the computer unit.

* * * * *